(12) United States Patent
Huwyler et al.

(10) Patent No.: US 6,903,129 B2
(45) Date of Patent: Jun. 7, 2005

(54) D-PROLINE PRODRUGS

(75) Inventors: Joerg Huwyler, Burg (CH); Roland Jakob-Roetne, Inzlingen (DE); Sonia Maria Poli, Basle (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/307,699

(22) Filed: Dec. 2, 2002

(65) Prior Publication Data

US 2003/0134891 A1 Jul. 17, 2003

(30) Foreign Application Priority Data

Dec. 14, 2001 (EP) ............................................. 01129793

(51) Int. Cl.$^7$ .................... C07D 267/22; C07D 207/00; C07D 281/18; A61K 31/40
(52) U.S. Cl. ....................... 514/411; 514/422; 540/455; 548/524
(58) Field of Search ......................... 548/524; 540/455; 514/411, 422

(56) References Cited

U.S. PATENT DOCUMENTS 5,691,336 A 11/1997 Dorn et al.
6,103,910 A 8/2000 Hertel et al.

FOREIGN PATENT DOCUMENTS

EP 915 088 5/1999

OTHER PUBLICATIONS

Bungaard, H., Drugs of the Future, 16, pp. 443–458 (1991).
Houston, J. B., Biochem. Pharmacol., 47, pp. 1469–1479 (1994).
Noursadeghi et al., Proc. Natl. Acad. Sci. USA, 97, pp. 14584–14589 (2000).
Anderson F.M., et al., Anti–Cancer Drug Design, vol. 15, pp. 119–126 (2000).

Primary Examiner—Bruck Kifle

(74) Attorney, Agent, or Firm—George W. Johnston; Patricia S. Rocha-Tramaloni

(57) ABSTRACT

The invention relates to compounds of formulas

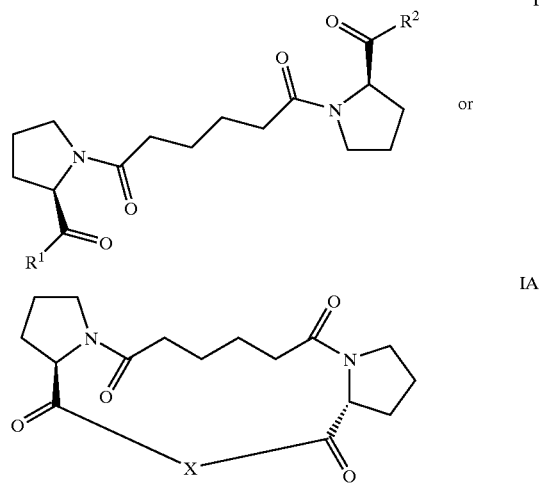

wherein
$R^1$ and $R^2$ are independently from each other lower alkoxy, lower alkenyloxy, benzyloxy, hydroxy, —OCH(CH$_3$)OC(O)-lower alkyl or —OCH$_2$C(O)N(R$^3$)(R$^4$), with the proviso that only one of $R^1$ or $R^2$ may be hydroxy;
$R^3$ and $R^4$ are independently from each other and signify hydrogen, lower alkyl, lower alkenyl or cycloalkyl; or
$R^1$ and $R^2$ form together with the carbon atom, to which they are attached the linking group X, wherein
X is —O(CH$_2$)$_n$CH=CH(CH$_2$)$_n$O— or —O(CH$_2$)$_m$O—;
n is 1, 2 or 3; and
m is 4–8, or
a pharmaceutically acceptable salt of said compound.

Compounds of the present invention can be used for the treatment of diseases where Serum Amyloid P Component depletion has a beneficial effect, in particular in the treatment or prevention of central and systemic amyloidosis.

13 Claims, No Drawings

D-PROLINE PRODRUGS

FIELD OF THE INVENTION

The present invention is concerned with new D-prolines of formulas

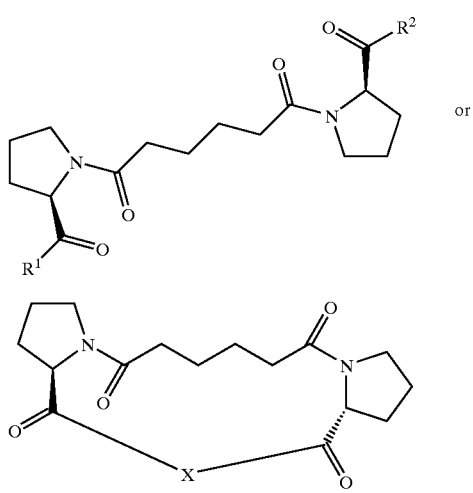

wherein
$R^1$ and $R^2$ are independently from each other lower alkoxy, lower alkenyloxy, benzyloxy, hydroxy, —OCH(CH$_3$)OC(O)-lower alkyl or —OCH$_2$C(O)N(R$^3$)(R$^4$), with the proviso that only one of $R^1$ or $R^2$ may be hydroxy;
$R^3$ and $R^4$ are independently from each other hydrogen, lower alkyl, lower alkenyl or cycloalkyl; or
$R^1$ and $R^2$ form together with the carbon atom, to which they are attached the linking group X, wherein
X is —O(CH$_2$)$_n$CH=CH(CH$_2$)$_n$O— or —O(CH$_2$)$_m$O—;
n is 1, 2 or 3; and
m is 4–8,
as well as pharmaceutically acceptable salts of said compounds.

BACKGROUND OF THE INVENTION

The D-proline of formula II (parent compound) is a known compound and is disclosed in EP 915 088. Formula II is provided as

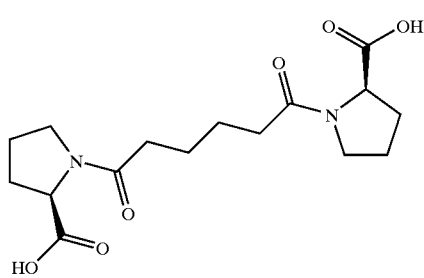

Compounds of formula II have a limited bioavailability. It was therefore useful to find derivatives of the compound of formula II to render these compounds suitable for oral application.

A molecule with optimal structural configuration and physicochemical properties for eliciting the desired therapeutic response at its target site does not necessarily possess the best molecular form and properties for delivery to its point of ultimate action. Usually, only a minor fraction of doses administered reach the target area and since most agents interact with non-target sites as well, an inefficient delivery may result in undesirable side effects. This fact of differences in transport and in situ effect characteristics for many drug moleculs is the fundamental reason why bioreversible chemical derivatization of drugs, i.e, prodrug formation, is a means by which a substantial improvement in the overall efficacy of drugs can be achieved.

Therefore, the prodrug approach involves
1. enhancement of bioavailability and passage through various biological barriers,
2. increased duration of pharmacological effects,
3. increased site-specificity,
4. decreased toxicity and adverse reactions,
5. improvement of organoleptic properties, and
6. improvement of stability and solubility.

A prodrug is a pharmacologically inactive derivative of a parent drug molecule that requires spontaneous or enzymatic transformation within the body in order to release the active drug, and that has improved delivery properties over the parent drug molecule. Prodrugs are designed to overcome pharmaceutically and/or pharmacokinetically based problems associated with the parent drug molecule that would otherwise limit the clinical usefulness of the drug.

In recent years several types of bioreversible derivatives have been exploited for designing prodrugs. Using esters as a prodrug type for drugs containing carboxyl or hydroxyl function is most popular. Further well-known are prodrug derivatives of peptides, 4-imidazolidinones and the like, described in *Drugs of the Future,* 1991, 16(5), 443–458 or N-oxides, described, for example, in U.S. Pat. No. 5,691,336.

It is desirable to provide novel compounds of formulas I and IA to overcome pharmaceutically and/or pharmacokinetically based problems associated with the parent drug molecule of formula II that would otherwise limit the clinical usefulness of the drug.

SUMMARY OF THE INVENTION

An aspect of the present invention is directed to a compound of formula I or IA, and their pharmaceutically acceptable salt.

Another embodiment of this invention is directed to a compound of formula I or IA for use as prodrug in the treatment or prevention of central and systemic amyloidosis.

Another embodiment of the present invention is directed to a pharmaceutical composition comprising one or more compounds of formula I and IA and a pharmaceutically acceptable excipient, particularly those suitable for the treatment of diseases related to central and systemic amyloidosis.

Yet another embodiment of this invention is directed to a method of treating diseases related to central and systemic amyloidosis comprising administering to a patient in need of such treatment a therapeutically effective amount of at least one compound of formula I or IA.

PREFERRED DESCRIPTION OF THE INVENTION

Compounds of the present invention can be used for the treatment of diseases where Serum Amyloid P Component depletion has a beneficial effect, in particular in the treatment or prevention of all forms of central and systemic amyloidosis. The most common disorders associated with amyloidosis are Alzheimer's disease, maturity onset diabetes mellitus or amyloidosis as a significant cause of non-ischaemic heart failure, as complication of long term haemodialysis in renal failure, as complication of monoclonal gammopathies, from chronic inflammatory disorders, from chronic infections, or from certain types of cancer.

Furthermore, amyloidosis comprises many different diseases such as forms of hereditary amyloidosis, and most commonly familial amyloid polyneuropathy (FAP), scrapie and Kreuzfeld-Jakob disease.

The compounds of the present invention may also be used in certain bacterial infections (M. Noursadeghi et. al., Proc. Natl.Acad. Sci. USA 97 (2000) 14584–14589).

It has now surprisingly been found that compounds of formulas I and IA were, in vitro and in vivo, readily converted to the parent compound of formula II

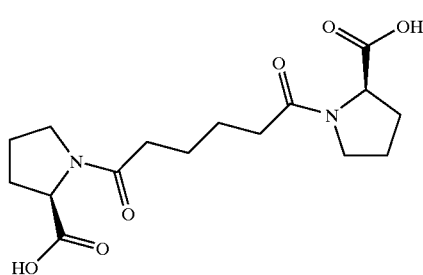

II and can therefore be used as prodrugs.

The most preferred embodiment of this invention is the prodrugs of formula I. Exemplarly preferred are compounds of formula I, wherein $R^1$ and $R^2$ are identical, $R^1$ and $R^2$ are —OCH$_2$C(O)N($R^3$)($R^4$) or lower alkoxy, and $R^3$ and $R^4$ are independently from each other hydrogen, lower alkyl, lower alkenyl or cycloalkyl.

Preferred compounds, wherein $R^1$ and $R^2$ are —OCH$_2$C(O)N($R^3$)($R^4$), are the followings:

(R)-1-[6-[(R)-2-carbamoylmethoxycarbonyl-pyrrolidin-1-yl]-6-oxo-hexanoyl]-pyrrolidine-2-carboxylic acid carbamoylmethyl ester, (R)-1-[6-[(R)-2-allylcarbamoylmethoxycarbonyl-pyrrolidin-1-yl]-6-oxo-hexanoyl]-pyrrolidine-2-carboxylic acid allylcarbamoylmethyl ester, (R)-1-{6-[(R)-2-(isopropylcarbamoyl-methoxycarbonyl)-pyrrolidin-1-yl]-6-oxo-hexanoyl}-pyrrolidine-2-carboxylic acid isopropylcarbamoyl-methyl ester, (R)-1-{6-[(R)-2-(tert-butylcarbamoyl-methoxycarbonyl)-pyrrolidin-1-yl]-6-oxo-hexanoyl}-pyrrolidine-2-carboxylic acid tert-butylcarbamoyl-methyl ester, (R)-1-{6-[(R)-2-(cyclopropylcarbamoyl-methoxycarbonyl)-pyrrolidin-1-yl]-6-oxo-hexanoyl}-pyrrolidine-2-carboxylic acid cyclopropylcarbamoyl-methyl ester, (R)-1-{6-[(R)-2-(dimethylcarbamoyl-methoxycarbonyl)-pyrrolidin-1-yl]-6-oxo-hexanoyl}-pyrrolidine-2-carboxylic acid dimethylcarbamoyl-methyl ester or (R)-1-{6-[(R)-2-(diethylcarbamoyl-methoxycarbonyl)-pyrrolidin-1-yl]-6-oxo-hexanoyl}-pyrrolidine-2-carboxylic acid diethylcarbamoyl-methyl ester.

Preferred compounds, wherein $R^1$ and $R^2$ are lower alkoxy, are the followings:

(R)-1-{6-[(R)-2-methoxycarbonyl-pyrrolidin-1-yl]-6-oxo-hexanoyl}-pyrrolidine-2-carboxylic acid methyl ester, (R)-1-{6-[(R)-2-ethoxycarbonyl-pyrrolidin-1-yl]-6-oxo-hexanoyl}-pyrrolidine-2-carboxylic acid ethyl ester or (R)-1-{6-oxo-6-[(R)-2-propoxycarbonyl-pyrrolidin-1-yl]-hexanoyl}-pyrrolidine-2-carboxylic acid propyl ester.

The invention relates further to compounds of formula IA, wherein X is

—O(CH$_2$)$_n$CH=CH(CH$_2$)$_n$O— or —O(CH$_2$)$_m$O—.

Compounds, wherein X is —O(CH$_2$)$_n$CH=CH(CH$_2$)$_n$O—, are the followings:

(12R,21R)-14,19-dioxa-1,8-diaza-tricyclo[19.3.0.0 8,12] tetracos-16-ene-2,7,13,20-tetraone, (12R,23R)-14,21-dioxa-1,8-diaza-tricyclo[21.3.0.0 8,12] hexacos-17-ene-2,7,13,22-tetraone or (12R,25R)-14,23-dioxa-1,8-diaza-tricyclo[23.3.0.0 8,12] octacos-18-ene-2,7,13,24-tetraone.

Compounds, wherein X is —O(CH$_2$)$_m$O— are for example the followings:

(12R,21R)-14,19-dioxa-1,8-diaza-tricyclo[19.3.0.0 8,12] tetracosane-2,7,13,20-tetraone, (12R,23R)-14,21-dioxa-1,8-diaza-tricyclo[21.3.0.0 8,12] hexacosane-2,7,13,22-tetraone or (12R,25R)-14,23-dioxa-1,8-diaza-tricyclo[23.3.0.0 8,12] octacosane-2,7,13,24-tetraone.

As used herein "pharmaceutically acceptable salts" useful in this invention include salts derived from metals, salts from amino acids and salts of mineral or organic acids. Examples of preferred metal salts are those derived from the alkali metals, for example, lithium (Li$^+$), sodium (Na$^+$) and potassium (K$^+$). Especially preferred is sodium. Other salts are derived from amino acids such as, for example, salts with arginine or lysine.

In the formulas represented herein, when substituents are illustrated as joined to the nucleus a solid line (———) indicates that the substituent is in the β-orientation, that is, above the plane of the molecule, a broken line (⋯⋯) indicates that the substituent is in the α-orientation, that is, below the plane of the molecule.

The term "lower alkyl" refers to both straight and branched chain saturated hydrocarbon groups having 1 to 6 and preferably 1 to 4 carbon atoms, for example, methyl, ethyl, n-propyl, isopropyl and tertiary butyl.

By the term "cycloalkyl" is meant a 3–6 membered saturated carbocyclic moiety, e.g., cyclopropyl, cyclobutyl, cyclopentyl and cyclohexyl, in particular cyclopentyl.

The compound of formula I or a salt thereof can be produced by methods known in the art. Moreover, a compound of formula I can be prepared by esterifying the compound of formula II or a salt thereof with a compound of formulas

Y—$R^5$    III wherein Y is a halogen atom, preferably a chlorine atom; $R^5$ is lower alkyl, lower alkenyl, benzyl, —CH(CH$_3$)OC(O)-lower alkyl or —CH$_2$C(O)N($R^3$)($R^4$); and $R^3$ and $R^4$ are described above.

In the esterification reaction, the starting compound III is used in a proportion of about 1 to 3 mole equivalents to each equivalent of the starting compound II or a salt thereof.

Examples of compounds of formula III are the followings: 2-chloroacetamide, N-(chloroacetyl)allylamine, N(chloroacetyl)isopropylamine, N-(chloroacetyl)-t-butylamine, N-(chloroacetyl)-cyclopropylamine, 2-chloro-N,N-dimethylacetamide, 2-chloro-N,N-diethylacetamide, 2-chloro-N,N-diisopropylacetamide or 2-chloro-N-t-butyl-N-methylacetamide.

This reaction is carried out in a solvent inert to the reaction. Suitable solvents include N,N-dimethylforamide, N,N-dimethylacetamide, acetone, and acetonitrile. Examples 1–9 have been prepared in this way.

The compound of formula I, wherein $R^1$ and $R^2$ are both methoxy (Example 10) may be prepared by a reaction of a Solution of diazomethane in diethylether with a solution of the compound of formula II in tetrahydrofuran.

Furthermore, compounds of Examples 11–16 have been prepared by reactions of a solution of a compound of formula II and Amberlite® IR120 (ion-exchange resin, useful in catalytic applications) in conventional manner with ethanol, propanol, butanol, allylalcohol, 3-buten-1-ol and 4-penten-1-ol.

The compound of formula I, wherein $R^1$ is ethoxy and $R^2$ is benzyloxy (Example 17) has been prepared from a mixture of adipic acid anhydride, D-proline-O-benzyl hydrochloride and N-methyl-morpholine in dichloromethane with a polymer bound primary amine and with a mixture of N-methyl-morpholin, 1-hydroxybenzotriazole, 1-(3-dimethylethylaminopropyl)-3-ethylcarbodiimide hydrochloride and H-D-Proline-O-ethyl.

The benzyloxy group may then be hydrogenated to the hydroxy group in the presence of palladium/carbon in ethylacetate (Example 18).

A compound of formula I, wherein $R^1$ and $R^2$ are both —OCH(CH$_3$)OC(O)-t-butyl (Example 19) maybe prepared from a solution of a compound of formula II with diazabicycloundecan with 2,2-dimethyl-propionic acid (RS)-1-bromo-ethyl ester at room temperature.

Further, a compound of formula IA may be prepared by reaction of (R)-1-{6-[(R)-2-alkoxycarbonyl-pyrrolidin-1-yl]-6-oxo-hexanoyl}-pyrrolidine-2-carboxylic acid allyl ester (Example 20), or (R)-1-{-[(R)-2-but-3-enyloxycarbonyl-pyrrolidin-1-yl]-6-oxo-hexanoyl}-pyrrolidine-2-carboxylic acid but-3-enyl ester (Example 21), or (R)-1-{6-[(R)-2-pent-4-enyloxycarbonyl-pyrrolidin-1-yl]-6-oxo-hexanoyl}-pyrrolidine-2-carboxylic acid pent-4-enyl ester (Example 22) with benzylidene-bis(tricyclohexylphosphine)-dichlororuthenium in dichloromethane. The reaction is carried out at about 50° C.

The double bond in compounds of Examples 20, 21 and 22 may then be hydrogenated with palladium/carbon in ethylacetate in conventional manner to compounds of Examples 23, 24 and 25.

As mentioned earlier, the compounds of formula I and their pharmaceutically usable addition salts may be used as prodrugs of the parent compounds of formula II, which possess valuable pharmacological properties.

These compounds were investigated in accordance with the test provided below.

The evidence, that the compounds of formula I may be used as prodrugs of their parent compounds of formula II is shown in accordance with the description given hereinafter.

The conversion of prodrugs to the corresponding parent compounds is via a hydrolytic mechanism and there is well known evidence from the literature that similar reactions occur in vivo.

Test Description
Stability of the Prodrugs in Blood and Plasma Samples

Plasma and blood samples from different species were merged with equimolar amounts (10 μM) of prodrug and parent drug in DMSO and incubated for different time intervals (up to 60 min.) at 37° C. The reaction was stopped by protein precipitation with acetonitrile followed by centrifugation (20 min., 1800 g at 10° C.). The supernatant was immediately subjected to analysis.

The concentration of formed parent compound was determined by LC-MS. The chromatographic system was comprised of a trapping column (X-Terra™ MS C8 3.5 μm, 10×2.1 mm i.d., Waters) and an analytical column (Symmetry C8 3.5 μm, 50×2.1 mm i.d., Waters) connected to a SCIEX API 2000 triplequadrupole mass spectrometer equipped with a turbo ion spray interface. The mobile phases were 1% aqueous formic acid and acetonitrile. The parent compound together with its deuterium labelled internal standard was enriched on the trapping column and eluted with a fast gradient. The retention time of (R)-1-[6-[(R)-2-carboxy-pyrrolidin-1-yl]-6-oxo-hexanoyl]-pyrrolidine-2-carboxylic acid was ~2.1 min. The effluent (300 μl min$^{-1}$) was passed to the turbo ion spray interface without splitting and was nebulized using nitrogen. Multiple reaction monitoring (MRM) in positive mode Was used for mass spectrometric detection. The transitions for the parent were 341.1 [M+H]$^+$ to 226.1 [Fragment]$^+$ and for the internal standard 349.1 [M+H]$^+$ to 234.1 [Fragment]$^+$. The results were expressed as half-lifes (50% conversion of the prodrug), using the data of the prodrug at time-point 0 min. as 0% value.

Test Description for Microsome Incubation

Rat and human liver microsome incubations were conducted on-line in a CTC PAL autosampler in order to avoid any degradation of the prodrugs during the work-up. Incubation mixtures consisted of liver microsomes (rat 1.0 mg prot/mL or human 2.0 mg prot/mL), prodrug 10 μM, MgCl$_2$ (3.3 mM), and an NADPH regenerating system consisting of glucose-6-phosphate dehydrogenase, NADPH and glucose-6-phosphate equivalent to 1 mM NADPH) in a total volume of 1.0 mL of potassium phosphate buffer 100 mM pH 7.4.

Reactions were initiated by addition of the NADPH regenerating system at 37° C. At time 1, 5, 9, 13, 17, 21, 25, and 29 min a 5 μL aliquot was directly analysed on a HPLC-MS/MS system comprising of a HP 1100 quaternary pump with degasser and a PE-Sciex API-2000 MS/MS spectrometer. The analytical column was a Waters Symmetry Shield RP8 (2.1*50 mm with a 3.5 μM particle size). A polarity non linear gradient from phase A (MeOH/Ac. Form.1% 20/80) to phase B (MeOH) was applied for a total run time of 2 minutes at a flow rate of 0.25 mL/min. The PE-Sciex API-2000 MS/MS spectrometer was used for detection of both the prodrugs and the parent compound (R)-1-[6-[(R)-2-carboxy-pyrrolidin-1-yl]-6-oxo-hexanoyl]-pyrrolidine-2-carboxylic acid. In vivo metabolic clearance was predicted according to published procedures (Houston, J. B., Biochem. Pharmacol., 47:1469–1479, 1994). In brief, the intrinsic clearance (Clearance, Table 1) was calculated from the measured in vitro half-life taking into account incubation volume and microsomal protein used for the in vitro incubation. The intrinsic clearance was expressed in terms of ul/min/mg microsomal protein. For in vivo extrapolations, the hepatic extraction ratio (E) was calculated. Reported below is the %MAB value (maximal achievable bioavailability), which is equal to 1−E.

Results

TABLE 1

| Example No. | Rat microsomes | | Human microsomes | | Rat plasma |
|---|---|---|---|---|---|
| | Clearance | MAB % | Clearance | MAB % | t1/2 hours |
| 1 | 5 | 88 | 1 | 93 | 0.4 |
| 2 | 18 | 66 | 64 | 20 | low |
| 3 | 82 | 30 | 16 | 50 | low |
| 4 | 625 | 5 | 57 | 22 | low |
| 5 | 36 | 50 | 8 | 67 | low |
| 6 | 7 | 84 | 1 | 96 | 0.8 |

TABLE 1-continued

| Example No. | Rat microsomes Clearance | MAB % | Human microsomes Clearance | MAB % | Rat plasma t1/2 hours |
|---|---|---|---|---|---|
| 7 | 9 | 73 | 2 | 90 | 0.2 |
| 10 | 9 | 79 | 2 | 90 | 1.3 |
| 11 | 46 | 44 | 5 | 77 | 0.4 |
| 12 | 253 | 12 | 73 | 18 | |

Table 1 shows that the compounds of formula I are potential prodrugs for the parent compound II.

It has been found, that the compounds of the formula I exhibit low stability in plasma where they give rise to the formation of the parent compound II. With microsomes they show a medium to low stability with the formation of compound II. The bioavailability was measured for selected examples: 12 (100%), 3 (8%), 5 (8%) and 13 (10%). For comparison, parent compound of formula II: 4%.

These findings suggest that the compounds of formula I show an increased oral bioavailability and therefore have potential value for the treatment of diseases where SAP depletion has a beneficial effect in particular as described above.

In accordance to the tests, the compounds of formula I can function as prodrugs of their parent compounds of formula II.

The compounds of formula I as well as their pharmaceutically usable acid addition salts can be used as medicaments or pharmaceutical composition, e.g., in the form of pharmaceutical preparations. The pharmaceutical preparations can be administered orally, e.g., in the form of tablets, coated tablets, dragées, hard and soft gelatine capsules, solutions, emulsions or suspensions. The administration can, however, also be effected rectally, e.g., in the form of suppositories, or parenterally, e.g., in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts can be used as such excipients e.g., for tablets, dragées and hard gelatine capsules.

Suitable excipients for soft gelatine capsules include vegetable oils, waxes, fats, semi-solid and liquid polyols.

Suitable excipients for the manufacture of solutions and syrups include water, polyols, saccharose, invert sugar and glucose.

Suitable excipients for injection solutions include water, alcohols, polyols, glycerol and vegetable oils.

Suitable excipients for suppositories are natural or hardened oils, waxes, fats, semi-liquid and liquid polyols.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples 1 to 25 illustrate the present invention without limiting it. All temperatures are given in decrees Celsius.

The following prodrugs have been prepared:

EXAMPLE 1

(R)-1-[6-[(R)-2-Carbamoylmethoxycarbonyl-pyrrolidin-1-yl]-6-oxo-hexanoyl]-pyrrolidine-2-carboxylic acid carbamoylmethyl ester

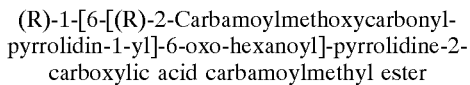

To a solution of 170 mg (0.5 mmol) (R)-1-[6-[(R)-2-carboxy-pyrrolidin-1-yl]-6-oxo-hexanoyl]-pyrrolidine-2-carboxylic acid and 93.5 mg (1 mmol) 2-chloroacetamide in 2 ml dimethylformamide were added 14.9 mg (0.1 mmol) sodium iodide and 139 ml (1 mmol) triethylamine. After stirring overnight at 90° C. the solvent was distilled off, the residue was taken up with dichloromethane and extracted with water, 2% aqueous sodium bicarbonate and brine. The organic extracts were dried with sodium sulfate and the solvent was distilled off to yield 100 mg (44%) of (R)-1-[6-[(R)-2-carbamoylmethoxycarbonyl-pyrrolidin-1-yl]-6-oxo-hexanoyl]-pyrrolidine-2-carboxylic acid carbamoylmethyl ester as a light yellow foam, MS m/e (%): 455 (M+H+, 100).

EXAMPLE 2

(R)-1-[6-[(R)-2-Allylcarbamoylmethoxycarbonyl-pyrrolidin-1-yl]-6-oxo-hexanoyl]-pyrrolidine-2-carboxylic acid allylcarbamoylmethyl ester

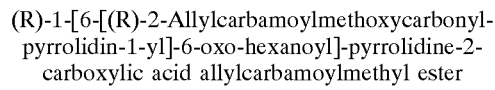

To a solution of 170 mg (0.5 mmol) (R)-1-[6-[(R)-2-carboxy-pyrrolidin-1-yl]-6-oxo-hexanoyl]-pyrrolidine-2-carboxylic acid and 134 mg (1 mmol) N-(chloroacetyl)allylamine in 3 ml dimethylformamide were added 14.9 mg (0.1 mmol) sodium iodide and 139 ml (1 mmol) triethylamine. After stirring, overnight at 90° C. the solvent was distilled off, the residue was taken up with dichloromethane and extracted with water. The organic extracts were dried with sodium sulfate and the solvent was distilled off to yield 200 mg (75%) of (R)-1-[6-[(R)-2-allylcarbamoylmethoxycarbonyl-pyrrolidin-1-yl]-6-oxo-hexanoyl]-pyrrolidine-2-carboxylic acid allylcarbamoylmethyl ester as a yellow oil, MS m/e (%): 535 (M+H+, 100).

EXAMPLE 3

(R)-1-{6-[(R)-2-(Isopropylcarbamoyl-methoxycarbonyl)-pyrrolidin-1-yl]-6-oxo-hexanoyl}-pyrrolidine-2-carboxylic acid isopropylcarbamoyl-methyl ester

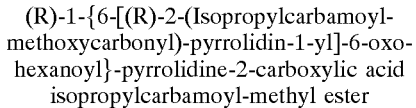

To a solution of 170 mg (0.5 mmol) (R)-1-[6-[(R)-2-carboxy-pyrrolidin-1-yl]-6-oxo-hexanoyl]-pyrrolidine-2-carboxylic acid and 136 mg (1 mmol) N-(chloroacetyl)isopropyl-amine in 3 ml dimethylformamide were added 14.9 mg (0.1 mmol) sodium iodide and 139 ml (1 mmol) triethylamine. After stirring overnight at 90° C. the solvent was distilled off, the residue was taken up with dichloromethane and extracted with water. The organic extracts were dried with sodium sulfate and the solvent was distilled off to yield 200 mg (74%) of (R)-1-{6-[(R)-2-(isopropylcarbamoyl-methoxycarbonyl)-pyrrolidin-1-yl]-6-oxo-hexanoyl}-pyrrolidine-2-carboxylic acid isopropylcarbamoyl-methyl ester as a yellow solid, MS m/e (%): 539 (M+H+, 100).

EXAMPLE 4

(R)-1-{6-[(R)-2-(tert-Butylcarbamoyl-methoxycarbonyl)-pyrrolidin-1-yl]-6-oxo-hexanoyl}-pyrrolidine-2-carboxylic acid tert-butylcarbamoyl-methyl ester

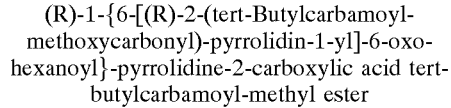

To a solution of 170 mg (0.5 mmol) (R)-1-[6-[(R)-2-carboxy-pyrrolidin-1-yl]-6-oxo-hexanoyl]-pyrrolidine-2- carboxylic acid and 149 mg (1 mmol) N-(chloroacetyl)-t-butyl-amine in 3 ml dimethylformamide were added 14.9 mg (0.1 mmol) sodium iodide and 139 ml (1 mmol) triethylamine. After stirring overnight at 90° C. the solvent was distilled off, the residue was taken up with dichloromethane and extracted with water. The organic extracts were dried with sodium sulfate and the solvent was distilled off to yield 205 mg (72%) of (R)-1-{6-[(R)-2-(tert-butylcarbamoyl-methoxycarbonyl)-pyrrolidin-1-yl]-6-oxo-hexanoyl}-pyrrolidine-2-carboxylic acid tert-butylcarbamoyl-methyl ester as a white solid, MS m/e (%): 567 (M+H+, 100).

EXAMPLE 5

(R)-1-{6-[(R)-2-(Cyclopropylcarbamoyl-methoxycarbonyl)-pyrrolidin-1-yl]-6-oxo-hexanoyl}-pyrrolidine-2-carboxylic acid cyclopropylcarbamoyl-methyl ester To a solution of 170 mg (0.5 mmol) (R)-1-[6-[(R)-2-carboxy-pyrrolidin-1-yl]-6-oxo-hexanoyl]-pyrrolidine-2-carboxylic acid and 134 mg (1 mmol) N-(chloroacetyl)-cyclopropyl-amine in 3 ml dimethylformamide were added 14.9 mg (0.1 mmol) sodium iodide and 139 ml (1 mmol) triethylamine. After stirring overnight at 90° C. the solvent was distilled off, the residue was taken up with dichloromethane and extracted with water. The organic extracts were dried with sodium sulfate and the solvent was distilled off to yield 190 mg (71%) of (R)-1-{6-[(R)-2-(cyclopropylcarbamoyl-methoxycarbonyl)-pyrrolidin-1-yl]-6-oxo-hexanoyl}-pyrrolidine-2-carboxylic acid cyclopropylcarbamoyl-methyl ester as a light yellow solid, MS m/e (%): 535 (M+H+, 100).

EXAMPLE 6

(R)-1-{6-[(R)-2-(Dimethylcarbamoyl-methoxycarbonyl)-pyrrolidin-1-yl]-6-oxo-hexanoyl}-pyrrolidine-2-carboxylic acid dimethylcarbamoyl-methyl ester To a solution of 170 mg (0.5 mmol) (R)-1-[6-[(R)-2-carboxy-pyrrolidin-1-yl]-6-oxo-hexanoyl]-pyrrolidine-2-carboxylic acid and 103 ml (1 mmol) 2-chloro-N,N-dimethylacetamide in 2.5 ml dimethylformamide were added 14.9 mg (0.1 mmol) sodium iodide and 139 ml (1 mmol) triethylamine. After stirring overnight at 100° C. the solvent was distilled off, the residue was taken up with dichloromethane and extracted with water. The organic extracts were dried with sodium sulfite and the solvent was distilled off to yield 190 mg (84%) of (R)-1-{6-[(R)-2-(dimethylcarbamoyl-methoxycarbonyl)-pyrrolidin-1-yl]-6-oxo-hexanoyl}-pyrrolidine-2-carboxylic acid dimethylcarbamoyl-methyl ester as a yellow oil, MS m/e (%): 511 (M+H+, 100).

EXAMPLE 7

(R)-1-{6-[(R)-2-(Diethylcarbamoyl-methoxycarbonyl)-pyrrolidin-1-yl]-6-oxo-hexanoyl}-pyrrolidine-2-carboxylic acid diethylcarbamoyl-methyl ester To a solution of 170 mg (0.5 mmol) (R)-1-[6-[(R)-2-carboxy-pyrrolidin-1-yl]-6-oxo-hexanoyl]-pyrrolidine-2-carboxylic acid and 137 ml (1 mmol) 2-chloro-N,N-diethylacetamide in 3 ml dimethylformamide were added 14.9 mg (0.1 mmol) sodium iodide and 139 ml (1 mmol) triethylamine. After stirring overnight at 90° C. the solvent was distilled off, the residue was taken up with dichloromethane and extracted with water. The organic extracts were dried with sodium sulfate and the solvent was distilled off to yield 260 mg (92%) of (R)-1-{6-[(R)-2-(diethylcarbamoyl-methoxycarbonyl)-pyrrolidin-1-yl]-6-oxo-hexanoyl}-pyrrolidine-2-carboxylic acid diethylcarbamoyl-methyl ester as a yellow oil, MS m/e (%): 567 (M+H+, 100).

EXAMPLE 8

(R)-1-{6-[(R)-2-(Diisopropylcarbamoyl-methoxycarbonyl)-pyrrolidin-1-yl]-6-oxo-hexanoyl}-pyrrolidine-2-carboxylic acid diisopropylcarbamoyl-methyl ester To a solution of 680 mg (2.0 mmol) (R)-1-[6-[(R)-2-carboxy-pyrrolidin-1-yl]-6-oxo-hexanoyl]-pyrrolidine-2-carboxylic acid and 708 mg (4 mmol) 2-chloro-N,N-diisopropylacetamide in 10 ml dimethylformamide were added 60.0 mg (0.4 mmol) sodium iodide and 557 ml (4 mmol) triethylamine. After stirring overnight at 90° C. the solvent was distilled off, the residue was taken up with dichloromethane and extracted with 2% aqueous sodium bicarbonate and brine. The organic extracts were dried with sodium sulfate and the solvent was distilled off to yield 885 mg (71%) of (R)-1-{6-[(R)-2-(diisopropylcarbamoyl-methoxycarbonyl)-pyrrolidin-1-yl]-6-oxo-hexanoyl}-pyrrolidine-2-carboxylic acid diisopropylcarbamoyl-methyl ester as an oil, MS m/e (%): 623 (M+H+, 100).

EXAMPLE 9

(R)-1-{6-[(R)-2-(tert-Butylmethylcarbamoyl-methoxycarbonyl)-pyrrolidin-1-yl]-6-oxo-hexanoyl}-pyrrolidine-2-carboxylic acid tert-butylmethylcarbamoyl-methyl ester To a solution of 680 mg (2.0 mmol) (R)-1-[6-[(R)-2-carboxy-pyrrolidin-1-yl]-6-oxo-hexanoyl]-pyrrolidine-2-carboxylic acid and 652 mg (4 mmol) 2-chloro-N-t-butyl-N-methylacetamide in 10 ml dimethylformamide were added 60.0 mg (0.4 mmol) sodium iodide and 557 ml (4 mmol) triethylamine. After stirring over the weekend at 90° C. the solvent was distilled off, the residue was taken up with dichloromethane and extracted with 2% aqueous sodium bicarbonate and brine. The organic extracts were dried with sodium sulfate and the solvent was distilled off to yield 1.02 g (85% ) of (R)-1-{6-[(R)-2-(tert-butylmethylcarbamoyl-methoxycarbonyl)-pyrrolidin-1-yl]-6-oxo-hexanoyl}-pyrrolidine-2-carboxylic acid tert-butylmethylcarbamoyl-methyl ester as a solid, MS m/e (%): 595 (M+H+, 100).

EXAMPLE 10

(R)-1-{6-[(R)-2-Methoxycarbonyl-pyrrolidin-1-yl]-6-oxo-hexanoyl}-pyrrolidine-2-carboxylic acid methyl ester A solution of diazomethane in diethylether (~6 mmol) was added to a solution of 500 mg (1.5 mmol) (R)-1-[6-[(R)-2-carboxy-pyrrolidin-1-yl]-6-oxo-hexanoyl]-pyrrolidine-2-carboxylic acid in 10 ml tetrahydrofuran. After stirring overnight methanol was added and the solvents were evaporated. The residue was taken up in dichloromethane, extracted with brine and dried with sodium sulfate. After separation from the solvent 400 mg (72%) (R)-1-{6-[(R) -2-methoxycarbonyl-pyrrolidin-1-yl]-6-oxo-hexanoyl}-pyrrolidine-2-carboxylic acid methyl ester were obtained as a light yellow oil, MS m/e (%): 369 (M+H+, 100).

EXAMPLE 11

(R)-1-{6-[(R)-2-Ethoxycarbonyl-pyrrolidin-1-yl]-6-oxo-hexanoyl}-pyrrolidine-2-carboxylic acid ethyl ester A mixture of 170 mg, (0.5 mmol) (R)-1-[6-[(R)-2-carboxy-pyrrolidin-1-yl]-6-oxo-hexanoyl]-pyrrolidine-2-carboxylic acid and 54 mg Amberlite® IR120 in 10 ml ethanol were stirred at room temperature for 48 hours. After filtration the solvent was distilled off, the residue was taken up in dichloromethane and extracted with 2% aqueous sodium bicarbonate. The organic extract was dried with sodium sulfate and the solvent was distilled off to yield 105 mg (53%) (R)-1-{6-[(R)-2-ethoxycarbonyl-pyrrolidin-1-yl]-6-oxo-hexanoyl}-pyrrolidine-2-carboxylic acid ethyl ester as alight yellow oil, MS m/e (%): 397 (M+H+, 100).

EXAMPLE 12

(R)-1-{6-Oxo-6-[(R)-2-propoxycarbonyl-pyrrolidin-1-yl]-hexanoyl}-pyrrolidine-2-carboxylic acid propyl ester A mixture of 170 mg (0.5 mmol) (R)-1-[6-[(R)-2-carboxy-pyrrolidin-1-yl]-6-oxo-hexanoyl]-pyrrolidine-2-carboxylic acid and 54 mg Amberlite® IR120 in 10 ml propanol were stirred at room temperature for 48 hours. After filtration the solvent was distilled off, the residue was taken up in dichloromethane and extracted with 2% aqueous sodium bicarbonate. The organic extract was dried with sodium sulfate and the solvent was distilled off to yield 65 mg (31%) (R)-1-{6-oxo-6-[(R)-2-propoxycarbonyl-pyrrolidin-1-yl]-hexanoyl}-pyrrolidine-2-carboxylic acid propyl ester as alight yellow oil, MS m/e (%): 424 (M+, 3), 268 (100), 156 (21), 70 (69).

EXAMPLE 13

(R)-1-{6-[(R)-2-Butoxycarbonyl-pyrrolidin-1-yl]-6-oxo-hexanoyl}-pyrrolidine-2-carboxylic acid butyl ester A mixture of 170 mg (0.5 mmol) (R)-1-[6-[(R)-2-carboxy-pyrrolidin-1-yl]-6-oxo-hexanoyl]-pyrrolidine-2-carboxylic acid and 54 mg Amberlite® IR120 in 10 ml butanol were stirred at room temperature for 48 hours. After filtration the solvent was distilled off, the residue was taken up in dichloroethane and extracted with 2% aqueous sodium bicarbonate. The organic extract was dried with sodium sulfate and the solvent was distilled off to yield 70 mg (31%) (R)-1-{6-[(R)-2-butoxycarbonyl-pyrrolidin-1-yl]-6-oxo-hexanoyl}-pyrrolidine-2-carboxylic acid butyl ester as alight yellow oil, MS m/e (%): 453 (M+H+, 100).

EXAMPLE 14

(R)-1-{6-[(R)-2-Alloxycarbonyl-pyrrolidin-1-yl]-6-oxo-hexanoyl}-pyrrolidine-2-carboxylic acid allyl ester A mixture of 1.02 g (3 mmol) (R)-1-[6-[(R)-2-carboxy-pyrrolidin-1-yl]-6-oxo-hexanoyl]-pyrrolidine-2-carboxylic acid and 3 g Amberlite® IR120 in 30 ml allylalcohol were stirred at room temperature for 90 hours. After filtration the solvent was distilled off, the residue was taken up in dichloromethane and extracted with 2% aqueous sodium bicarbonate. The organic extract was dried with sodium sulfate and the solvent was distilled off to yield 620 mg (49%) (R)-1-{6-[(R)-2-alloxycarbonyl-pyrrolidin-1-yl]-6-oxo-hexanoyl}-pyrrolidine-2-carboxylic acid allyl ester as alight yellow oil, MS m/e (%): 421 (M+H+, 100).

EXAMPLE 15

(R)-1-[6-[(R)-2-But-3-enyloxycarbonyl-pyrrolidin-1-yl]-6-oxo-hexanoyl]-pyrrolidin-2-carboxylic acid but-3-enyl ester A mixture of 1.02 g (3 mmol) (R)-1-[6-[(R)-2-carboxy-pyrrolidin-1-yl]-6-oxo-hexanoyl]-pyrrolidine-2-carboxylic acid and 3 g Amberlite® IR120 in 25 ml 3-buten-1-ol were stirred at room temperature for 72 hours. After filtration the solvent was distilled off, the residue was taken up in dichloromethane and extracted with 2% aqueous sodium bicarbonate. The organic extract was dried with sodium sulfate and the solvent was distilled off to yield 490 mg (37%) (R)-1-[6-[(R)-2-but-3-enyloxycarbonyl-pyrrolidin-1-yl]-6-oxo-hexanoyl]-pyrrolidine-2-carboxylic acid but-3-enyl ester as alight yellow oil, MS m/e (%): 449 (M+H+, 100).

EXAMPLE 16

(R)-1-[6-[(R)-2-Pent-4-enyloxycarbonyl-pyrrolidin-1-yl]-6-oxo-hexanoyl]-pyrrolidine-2-carboxylic acid pent-4-enyl ester A mixture of 2.04 g (6 mmol) (R)-1-[6-[(R)-2-carboxy-pyrrolidin-1-yl]-6-oxo-hexanoyl]-pyrrolidine-2-carboxylic acid and 5 g Amberlite® IR120 in 25 ml 4-penten-1-ol were stirred at room temperature for 48 hours. After filtration the solvent was distilled off, the residue was taken up in dichloromethane and extracted with 2% aqueous sodium bicarbonate. The organic extract was dried with sodium sulfate and the solvent was distilled off to yield 1.6 g (58%) (R)-1-[6-[(R)-2-pent-4-enyloxycarbonyl-pyrrolidin-1-yl]-6-oxo-hexanoyl]-pyrrolidine-2-carboxylic acid pent-4-enyl ester as a light yellow oil, MS m/e (%): 477 (M+H+, 100).

EXAMPLE 17

(R)-1-[6-[(R)-2-Ethoxycarbonyl-pyrrolidin-1-yl]-6-oxo-hexanoyl]-pyrrolidine-2-carboxylic acid benzyl ester A mixture of 403 mg (3.15 mmol) adipic acid anhydride, 604 mg (2.5 mmol) D-proline-benzyl-ester hydrochloride and 274 ml (2.5 mmol) N-methyl-morpholin in 10 ml dichloromethane was stirred at room temperature for 1 hour. Then 0.5 g polymer bound primary amine (2 meq/g) were added and stirring was continued for 1 hour. After filtration 823 ml (7.5 mmol) N-methyl-morpholin, 338 mg (2.5 mmol) 1-hydroxybenzotriazole, 479 mg (2.5 mmol) 1-(3-dimethylaminopropyl)-3-ethylcarbodiimide hydrochloride and 450 mg (2.5 mmol) D-proline-ethyl-ester were added and the mixture was stirred for another 48 hours. Removal of the solvent and chromatography on silicagel with ethylacetate gave 135 mg (12%) (R)-1-[6-[(R)-2-ethoxycarbonyl-pyrrolidin-1-yl]-6-oxo-hexanoyl]-pyrrolidine-2-carboxylic acid benzyl ester as a light yellow oil, MS m/e (%): 459 (M+H+, 100).

EXAMPLE 18

(R)-1-[6-[(R)-2-Ethoxycarbonyl-pyrrolidin-1-yl]-6-oxo-hexanoyl]-pyrrolidine-2-carboxylic acid A mixture of 92 mg (0.2 mmol) (R)-1-[6-[(R)-2-ethoxycarbonyl-pyrrolidin-1-yl]-6-oxo-hexanoyl]- pyrrolidine-2-carboxylic acid benzyl ester and 30 mg 10% palladium/carbon in 5 ml ethylacetate was hydrogenated over night. Filtration and removal of the solvent yielded 70 mg (R)-1-[6[(R)-2-ethoxycarbonyl-pyrrolidin-1-yl]-6-oxo-hexanoyl]-pyrrolidine-2-carboxylic acid as a light yellow oil, MS m/e (%): 369 (M+H+, 100).

EXAMPLE 19

(R)-1-(6-{(R)-2-[1-(2,2-Dimethyl-propionyloxy)-ethoxycarbonyl]-pyrrolidin-1-yl}-6-oxo-hexanoyl)-pyrrolidine-2-carboxylic acid 1-(2,2-dimethyl-propionyloxy)-ethyl ester (mixture of diastereomers)

To a solution of 170 mg (0.5 mmol) (R)-1-[6-[(R)-2-carboxy-pyrrolidin-1-yl]-6-oxo-hexanoyl]-pyrrolidine-2-carboxylic acid and 149 ml (1 mmol) diazabicycloundecan in 4 ml dimethylformamide were added 209 mg (1 mmol) 2,2-dimethyl-propionic acid (RS)-1-bromo-ethyl ester and the mixture was stirred at room temperature for 3 hours. The solvent was distilled off and the residue was taken up in water and extracted with dichloromethane. The organic extracts were washed with 2% aqueous sodium bicarbonate and buffer pH7 and dried with sodium sulfate. Removal of the solvent and chromatography on silicagel with ethylacetate gave 55 mg (18%) (R)-1-(6-{(R)-2-[1-(2,2-dimethyl-propionyloxy)-ethoxycarbonyl]-pyrrolidin-1-yl}-6-oxo-hexanoyl)-pyrrolidine-2-carboxylic acid 1-(2,2-dimethyl-propionyloxy)-ethyl ester (mixture of diastereomers) as a colorless oil, MS m/e (%): 597 (M+H+, 100).

EXAMPLE 20

(12R,21R)-14,19-Dioxa-1,8-diaza-tricyclo[19.3.0.0 8,12]tetracos-16-ene-2,7,13,20-tetraone A mixture of 420 mg (1 mmol) (R)-1-{6[-(R)-2-alloxycarbonyl-pyrrolidin-1-yl]-6-oxo-hexanoyl}-pyrrolidine-2-carboxylic acid allyl ester and 40 mg benzylidene-bis(tricyclohexylphosphine)dichlororuthenium in 30 ml dry dichloromethane was stirred at 50° C. overnight. Removal of the solvent and chromatography on silicagel with ethylacetate/acetone with a ratio of 8/2 gave 110 mg (28%) (12R,21R)-14,19-dioxa-1,8-diaza-tricyclo[19.3.0.0 8,12]tetracos-16-ene-2,7,13,20-tetraone as light yellow oil, MS m/e (%): 393 (M+H+, 100).

EXAMPLE 21

(12R,23R)-14,21-Dioxa-1,8-diaza-tricyclo[21.3.0.0 8,12]hexacos-17-ene-2,7,13,22-tetraone A mixture of 410 mg (0.92 mmol) (R)-1-[6-[(R)-2-but-3-enyloxycarbonyl-pyrrolidin-1-yl]-6-oxo-hexanoyl]-pyrrolidine-2-carboxylic acid but-3-enyl ester and 40 mg benzylidene-bis(tricyclohexylphosphine)dichlororuthenium in 30 ml dry dichloromethane was stirred at 50° C. overnight. Removal of the solvent and chromatography on silicagel with ethylacetate/acetone with a ratio of 8/2 gave 200 mg (51%) (12R,23R)-14,21-dioxa-1,8-diaza-tricyclo[21.3.0.0 8,12]hexacos-17-ene-2,7,13,22-tetraone as an oil, MS m/e (%): 421 (M+H+, 100).

EXAMPLE 22

(12R,25R)-14,23-Dioxa-1,8-diaza-tricyclo[23.3.0.0 8,12]octacos-18-ene-2,7,13,24-tetraone A mixture of 1.20 g (2.5 mmol) (R)-1-[6-[(R)-2-pent-4-enyloxycarbonyl-pyrrolidin-1-yl]-6-oxo-hexanoyl]-pyrrolidine-2-carboxylic acid pent-4-enyl ester and 40 mg benzylidene-bis(tricyclohexylphosphine)dichlororuthenium in 30 ml dry dichloromethane was stirred at 50° C. overnight. Removal of the solvent and chromatography on silicagel with ethylacetate/acetone with a ratio of 8/2 gave 430 mg (38%) (12R,25R)-14,23-dioxa-1,8-diaza-tricyclo[23.3.0.0 8,12]octacos-18-ene-2,7,13,24-tetraone as an oil, MS m/e (%): 449 (M+H+, 100).

EXAMPLE 23

(12R,21R)-14,19-Dioxa-1,8-diaza-tricyclo[19.3.0.0 8,12]tetracosane-2,7,13,20-tetraone A mixture of 260 mg (0.66 mmol) (12R,21R)-14,19-dioxa-1,8-diaza-tricyclo[19.3.0.0 8,12]tetracos-16-ene-2,7,13,20-tetraone and 30 mg 10% palladium/carbon in 10 ml ethylacetate was hydrogenated over night. Filtration and removal of the solvent yielded 255 mg (98%) (12R,21R)-14,19-dioxa-1,8-diaza-tricyclo[19.3.0.0 8,12]tetracosane-2,7,13,20-tetraone as a light yellow oil, MS m/e (%): 395 (M+H+, 100).

EXAMPLE 24

(12R,23R)-14,21-Dioxa-1,8-diaza-tricyclo[21.3.0.0 8,12]hexacosane-2,7,13,22-tetraone A mixture of 150 mg (0.36 mmol) (12R,23R)-14,21-dioxa-1,8-diaza-tricyclo[21.3.0.0 8,12]hexacos-17-ene-2,7,13,22-tetraone and 20 mg 10% palladium/carbon in 5 ml ethylacetate was hydrogenated over night. Filtration and removal of the solvent yielded 120 mg (79%) (12R,23R)-14,21-dioxa-1,8-diaza-tricyclo[21.3.0.0 8,12]hexacosane-2,7,13,22-tetraone as a light yellow oil, MS m/e (%): 423 (M+H+, 100).

EXAMPLE 25

(12R,25R)-14,23-Dioxa-1,8-diaza-tricyclo[23.3.0.0 8,12]octacosane-2,7,13,24-tetraone A mixture of 400 mg (0.9 mmol) (12R,25R)-14,23-dioxa-1,8-diaza-tricyclo[23.3.0.0 8,12]octacos-18-ene-2,7,13,24-tetraone and 40 mg 10% palladium/carbon in 10 ml ethylacetate was hydrogenated over night. Filtration and removal of the solvent yielded 245 mg (61%) (12R,25R)-14,23-dioxa-1,8-diaza-tricyclo[23.3.0.0 8,12]octacosane-2,7,13,24-tetraone as a white solid, MS m/e (%): 451 (M+H+, 100).

EXAMPLE A

Tablets of the following composition are manufactured:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository molds of suitable size, left to cool, the suppositories are then removed from the molds and packed individually in wax paper or metal foil.

EXAMPLE D

An injection solution may have the following composition and is manufactured:

| Active substance | 1.0 mg |
|---|---|
| 1 n HCl | 20.0 µl |
| acetic acid | 0.5 mg |
| NaCl | 8.0 mg |
| phenol | 10.0 mg |
| 1 n NaOH | q.s. ad pH 5 |
| H$_2$O | q.s. ad 1 ml |

What is claimed is:

1. A compound of formula

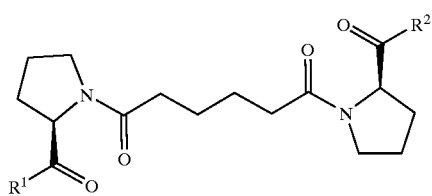

I wherein

R$^1$ and R$^2$ are independently from each other lower alkoxy, lower alkenyloxy, hydroxy, —OCH(CH$_3$)OC(O)-lower alkyl or —OCH$_2$C(O)N(R$^3$)(R$^4$), with the proviso that only one of R$^1$ or R$^2$ may be hydroxy;

R$^3$ and R$^4$ are independently from each other hydrogen, lower alkyl, lower alkenyl or cycloalkyl; or R$^1$ and R$^2$ form together with the carbon atom, to which they are attached the linking group X, wherein X is —O(CH$_2$)$_n$CH=CH(CH$_2$)$_n$O— or —O(CH$_2$)$_m$O—;

n is 1, 2 or 3; and m is 4–8;

or a pharmaceutically acceptable salt thereof.

2. The compound of formula I in accordance with claim 1, wherein R$^1$ and R$^2$ are identical.

3. The compound of formula I in accordance with claim 2, wherein R$^1$ and R$^2$ are both —OCH$_2$C(O)N(R$^3$)(R$^4$) and R$^3$ and R$^4$ are independently from each other hydrogen, lower alkyl, lower alkenyl or cycloalkyl.

4. The compound of formula I in accordance with claim 3, wherein the compound is (R)-1-[6-[(R)-2-carbamoylmethoxycarbonyl-pyrrolidin-1-yl]-6-oxo-hexanoyl]-pyrrolidine-2-carboxylic acid carbamoylmethyl ester, (R)-1-[6-[(R)-2-allylcarbamoylmethoxycarbonyl-pyrrolidin-1-yl]-6-oxo-hexanoyl]-pyrrolidine-2-carboxylic acid allylcarbamoylmethyl ester, (R)-1-{6-[(R)-2-(isopropylcarbamoyl-methoxycarbonyl)-pyrrolidin-1-yl]-6-oxo-hexanoyl}-pyrrolidine-2-carboxylic acid isopropylcarbamoyl-methyl ester, (R)-1-{6-[(R)-2-(tert-butylcarbamoyl-methoxycarbonyl)-pyrrolidin-1-yl]-6-oxo-hexanoyl}-pyrrolidine-2-carboxylic acid tert-butylcarbamoyl-methyl ester, (R)-1-{6-[(R)-2-(cyclopropylcarbamoyl-methoxycarbonyl)-pyrrolidin-1-yl]-6-oxo-hexanoyl}-pyrrolidine-2-carboxylic acid cyclopropylcarbamoyl-methyl ester, (R)-1-{6-[(R)-2-(dimethylcarbamoyl-methoxycarbonyl)-pyrrolidin-1-yl]-6oxo-hexanoyl}-pyrrolidine-2-carboxylic acid dimethylcarbamoyl-methyl ester or (R)-1-{6-[(R)-2-(diethylcarbamoyl-methoxycarbonyl)-pyrrolidin-1-yl]-6-oxo-hexanoyl}-pyrrolidine-2-carboxylic acid diethylcarbamoyl-methyl ester.

5. The compound of formula I in accordance with claim 2, wherein R$^1$ and R$^2$ are both lower alkoxy.

6. The compound of formula I in accordance with claim 5, wherein the compound is (R)-1-{6-[(R)-2-methoxycarbonyl-pyrrolidin-1-yl]-6-oxo-hexanoyl}-pyrrolidine-2-carboxylic acid methyl ester, (R)-1-{6-[(R)-2-ethoxycarbonyl-pyrrolidin-1-yl]-6-oxo-hexanoyl}-pyrrolidine-2-carboxylic acid ethyl ester or (R)-1-{6-oxo-6-[(R)-2-propoxycarbonyl-pyrrolidin-1-yl]-hexanoyl}-pyrrolidine-2-carboxylic acid propyl ester.

7. A compound of formula

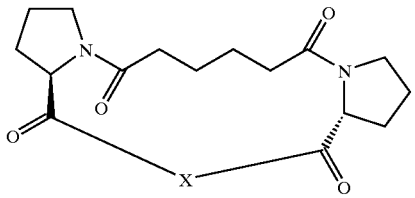

IA wherein X is —O(CH$_2$)$_n$CH=(CH$_2$)$_n$O— or —O(CH$_2$)$_m$O—;

n is 1, 2 or 3; and m is 4 to 8;

or a pharmaceutically acceptable salt thereof.

8. The compound in accordance with claim 7, wherein X is —O(CH$_2$)$_n$CH=CH(CH$_2$)$_n$O—.

9. The compound in accordance with claim 8, wherein the compound is (12R,21R)-14,19-dioxa-1,8-diaza-tricyclo[19.3.0.0 8,12] tetracos-16-ene-2,7,13,20-tetraone, (12R,23R)-14,21-dioxa-1,8-diaza-tricyclo[21.3.0.0 8,12] hexacos-17-ene-2,7,13,22-tetraone or (12R,25R)-14,23-dioxa-1,8-diaza-tricyclo[23.3.0.0 8,12] octacos-18-ene-2,7,13,24-tetraone.

10. The compound of formula IA in accordance with claim 7, wherein X is —O(CH$_2$)$_m$O—.

11. The compound of formula IA in accordance with claim 10, wherein the compound is (12R,21R)-14,19-dioxa-1,8-diaza-tricyclo[9.3.0.0 8,12] tetracosane-2,7,13,20-tetraone, (12R,23R)-14,21-dioxa-1,8-diaza-tricyclo[21.3.0.0 8,12] hexacosane-2,7,13,22-tetraone or (12R,25R)-14,23-dioxa-1,8-diaza-tricyclo[23.3.0.0 8,12] octacosane-2,7,13,24-tetraone.

12. A pharmaceutical composition comprising one or more compounds of formula I

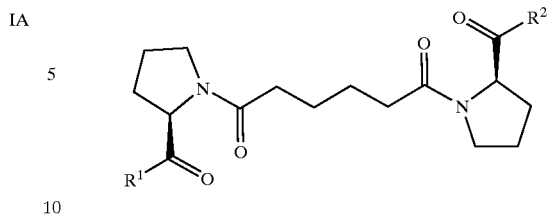

I wherein

R$^1$ and R$^2$ are independently from each other lower alkoxy, lower alkenyloxy, hydroxy, —OCH(CH$_3$)OC(O)-lower alkyl or —OCH$_2$C(O)N(R$^3$)(R$^4$), with the proviso that only one of R$^1$ or R$^2$ may be hydroxy;

R$^3$ and R$^4$ are independently from each other hydrogen, lower alkyl, lower alkenyl or cycloalkyl; or R$^1$ and R$^2$ form together with the carbon atom, to which they are attached the linking group X, wherein X is —O(CH$_2$)$_n$CH=CH(CH$_2$)$_n$O— or —O(CH$_2$)$_m$O—;

n is 1, 2 or 3; and m is 4–8 and a pharmaceutically acceptable excipient.

13. A pharmaceutical composition comprising one or more compounds of formula IA

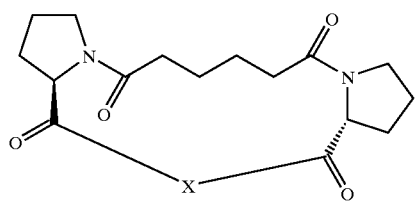

IA wherein X is —O(CH$_2$)$_n$CH=(CH$_2$)$_n$O— or —O(CH$_2$)$_m$O—;

n is 1, 2 or 3; and m is 4 to 8 and a pharmaceutically acceptable excipient.

* * * * *

UNITED STATES PATENT AND TRADEMARK OFFICE
CERTIFICATE OF CORRECTION

PATENT NO. : 6,903,129 B2
DATED : June 7, 2005
INVENTOR(S) : Huwyler et al.

It is certified that error appears in the above-identified patent and that said Letters Patent is hereby corrected as shown below:

Title page,
Item [73], Assignee, "Hoffman-La Roche Inc., Nutley, NJ" should be
-- Hoffmann-La Roche Inc., Nutley, NJ --.

Signed and Sealed this

Sixth Day of September, 2005

JON W. DUDAS
*Director of the United States Patent and Trademark Office*